United States Patent
Suzuki et al.

(10) Patent No.: US 8,263,529 B2
(45) Date of Patent: Sep. 11, 2012

(54) HERBICIDE COMPOSITION

(75) Inventors: Tadayuki Suzuki, Wakayama (JP); Akio Manba, Wakayama (JP); Herry Prasetyo, West Java (ID); Ferry Hermawanto, West Java (ID); Suharyanto, West Java (ID); Sri Muljati, West Java (ID)

(73) Assignee: Kao Corporation, Tokyo (JP)

(*) Notice: Subject to any disclaimer, the term of this patent is extended or adjusted under 35 U.S.C. 154(b) by 814 days.

(21) Appl. No.: 11/658,998

(22) PCT Filed: Sep. 27, 2005

(86) PCT No.: PCT/JP2005/018254
§ 371 (c)(1),
(2), (4) Date: Dec. 19, 2008

(87) PCT Pub. No.: WO2006/035983
PCT Pub. Date: Apr. 6, 2006

(65) Prior Publication Data
US 2009/0149328 A1 Jun. 11, 2009

(30) Foreign Application Priority Data
Sep. 27, 2004 (JP) .................................. 2004-278837

(51) Int. Cl.
*A01N 37/00* (2006.01)
*A01N 25/02* (2006.01)
*A01N 25/00* (2006.01)
*A61K 47/00* (2006.01)

(52) U.S. Cl. ......... 504/142; 504/362; 514/772; 514/975
(58) Field of Classification Search .................. 504/142, 504/362; 514/772, 975
See application file for complete search history.

(56) References Cited

U.S. PATENT DOCUMENTS

| | | | |
|---|---|---|---|
| 5,739,106 A | 4/1998 | Rink et al. | |
| 5,767,056 A * | 6/1998 | Lenoir | 510/423 |
| 5,888,934 A | 3/1999 | Townson et al. | |
| 6,127,318 A | 10/2000 | Sato et al. | |
| 6,313,074 B1 * | 11/2001 | Suzuki et al. | 504/362 |
| 2005/0037924 A1 * | 2/2005 | Massmann et al. | 504/206 |
| 2006/0178440 A1 * | 8/2006 | Blease | 516/77 |

FOREIGN PATENT DOCUMENTS

| | | | |
|---|---|---|---|
| JP | 7-223912 A | | 8/1995 |
| JP | 09-506615 A | | 6/1997 |
| JP | 10-502071 A | | 2/1998 |
| JP | 11-035406 A | | 2/1999 |
| JP | 11-147927 A | | 6/1999 |
| JP | 11-507637 A | | 7/1999 |
| JP | 2002-510605 A | | 4/2002 |
| WO | WO95/16351 | * | 6/1995 |
| WO | WO-95/16351 A1 | | 6/1995 |
| WO | WO-96/00010 A1 | | 1/1996 |
| WO | WO-97/00010 A1 | | 1/1997 |
| WO | WO-99/03345 A1 | | 1/1999 |
| WO | WO-00/42847 | | 7/2000 |
| WO | WO-00/64256 A1 | | 11/2000 |
| WO | WO-03/082009 A1 | | 10/2003 |

OTHER PUBLICATIONS

Japanese Notice of Final Rejection dated Oct. 18, 2011 for Japanese Application No. 2005-275135.
Office Action in European Application No. 05787521.3, dated Jan. 12, 2012.
Computer generated English translation of JP 7-223912 A published Aug. 22, 1995.
Japanese Office Action mailed on Mar. 8, 2011 in corresponding Japanese Patent Application No. 2005-275135 with its English translation.

* cited by examiner

*Primary Examiner* — Johann Richter
*Assistant Examiner* — Jane C Oswecki
(74) *Attorney, Agent, or Firm* — Birch, Stewart, Kolasch & Birch, LLP

(57) ABSTRACT

The invention relates to a herbicide composition containing (A) an amino acid-based herbicide and (B) a compound having a branched structure represented by formula (1):

$$R^1CH_2O-(R^2O)_nH \qquad (1)$$

wherein $R^1$ represents a C3 to C29 branched alkyl or branched alkenyl group, $R^2$ represents a C2 to C4 alkylene group, and n is a mean number in the range of 1 to 30.

11 Claims, No Drawings

HERBICIDE COMPOSITION

FIELD OF THE INVENTION

The present invention relates to a herbicide composition containing an amino acid-based herbicide.

BACKGROUND OF THE INVENTION

Agrochemicals including herbicides are used in the form of preparations such as emulsion, wettable powder, particle or granule, powder, flowable etc. For sufficiently bringing out the effect of raw agrochemicals, various measures have been made for physical properties of preparation forms, but under the present circumstances, further enhancement of the effect of agrochemicals by devising pharmaceutical forms is difficult. Because development of novel agrochemicals is further difficult, further enhancement of the activity of existing agrochemicals would be significantly meaningful in industry. For example, JP-A (W) 9-506615 discloses use of specific secondary or tertiary alcohol-based surfactants in order to improve rain resistance of herbicides such as glyphosate. JP-A 11-35406 (=WO99/03345) discloses that an alkylene oxide adduct of specific structure is used as an enhancer of the efficacy of various agrochemicals including herbicides.

SUMMARY OF THE INVENTION

The present invention relates to a herbicide composition containing (A) an amino acid-based herbicide [referred to hereinafter as component (A)] and (B) a compound represented by the following general formula (1) [referred to hereinafter as component (B)]:

$$R^1CH_2O-(R^2O)_nH \quad (1)$$

wherein $R^1$ represents a C3 to C29 branched alkyl or branched alkenyl group, $R^2$ represents a C2 to C4 alkylene group, and n is a mean number in the range of 1 to 30.

The present invention also relates to an efficacy enhancer for a herbicide, which contains a compound represented by the general formula (1) or an efficacy enhancer composition for a herbicide, which containing the same.

The present invention also relates to a method of weeding by applying the herbicide composition onto a plant to be controlled, use of the herbicide composition as a herbicide, a method of enhancing the efficacy of a herbicide by the compound (B) or a composition containing the same, or use of the compound (B) or a composition containing the same in enhancing the efficacy of a herbicide.

DETAILED DESCRIPTION OF THE INVENTION

Improvements in wetting properties and permeability of herbicides are advantageous in enhancing their weeding effect, but sufficient improvements in wetting properties and permeability of herbicides, particularly amino acid-based herbicides, are difficult even if the compounds described in the patent literatures mentioned above are used.

[Former Part of the Abstract]

The present invention provides a herbicide composition containing an amino acid-based herbicide excellent in wetting properties and permeability and also in a weeding effect.

According to the present invention, there is obtained a herbicide composition excellent in wetting properties and permeability and also in a weeding effect.

<Component (A)>

The active ingredient (agrochemical material) of the amino acid-based herbicide includes glyphosate [N-(phosphonomethyl)glycine or its salt], Bialaphos [sodium salt of L-2-amino-4-[(hydroxy) (methyl) phosphinoyl] butyryl-L-alanyl-L-alanine] and gluphosinate [ammonium-DL-homoalanin-4-yl(methyl) phoshinate], and these may be agriculturally acceptable salts. For incorporation into the composition, an aqueous solution, a liquid, a wettable powder etc. containing these active ingredients can be used.

<Component (B)>

The component (B) is a compound represented by the general formula (1) above.

In the component (B) of the general formula (1), $R^1$ is preferably a C5 to C29 branched alkyl or branched alkenyl group, particularly preferably a C7 to C21 branched alkyl group. $R^2$s are preferably C2 and C3 alkylene groups or C2 alkylene groups, and n is a mean number in the range of 6 to 20.

The compound (B) is preferably a compound represented by the following general formula (1'):

$$R^1CH_2O-(R^{2a}O)_j(R^{2b}O)_kH \quad (1')$$

wherein $R^1$ represents a C3 to C29 branched alkyl or branched alkenyl group, $R^{2a}$ and $R^{2b}$ each represent a C2 to C4 alkylene group, and are not simultaneously the same, j and k each represent a mean number in the range of 0 to 30, and are not simultaneously 0, and j+k=1 to 30.

In the formula, $-(R^2O)_n-$ or $-(R^{2a}O)_j(R^{2b}O)_k-$ is preferably one or two blocks of an oxyethylene group and/or an oxypropylene group.

In the component (B) of the general formula (1), $R^1CH_2-$ is preferably a C6 to C30 branched alkyl or branched alkenyl group, more preferably a C8 to C22 branched alkyl group. The branched chain type of $R^1CH_2-$ is Guerbet, iso, multi-branch, more preferably Guerbet or iso, still more preferably Guerbet. Specific examples of $R^1CH_2-$ include a 2-ethylhexyl group, isotridecyl group, isodecyl group, C28 Guerbet-alkyl group, isostearyl group, 2-octyldodecyl group etc., among which the 2-ethylhexyl group, isotridecyl group and isodecyl group are preferable, and particularly the 2-ethylhexyl group is preferable. $R^{2a}O$ and $R^{2b}O$ are added in a block form, and are preferably a C2 oxyalkylene group (also called an oxyethylene group)/C3 oxyalkylene (also called an oxypropylene group) mixture or C2 oxyalkylene groups. It is particularly preferable that $R^{2a}$ is a C3 alkylene group and $R^{2b}$ is a C2 alkylene group, or $R^{2a}$ or $R^{2b}$ is a C2 alkylene group. j+k is a mean value preferably in the range of 6 to 20.

<Herbicide Composition>

The herbicide composition of the present invention contains the component (A) in an amount of preferably 0.1 to 80% by weight, more preferably 1 to 60% by weight as an agrochemical material (herbicidal active ingredient) contained in an amino acid-based herbicide. The component (B) is contained in an amount of preferably 0.01 to 50% by weight, more preferably 0.1 to 20% by weight.

The herbicide composition of the present invention is prepared by suitably selecting the type and amount of the active ingredient incorporated, depending on conditions in an application place, etc. For example, the herbicide composition of the present invention contains the active ingredients in a total amount [total amount of the component (A) (as raw material) and the component (B)] of preferably 0.1 to 90% by weight, more preferably 0.5 to 80% by weight, still more preferably 1 to 70% by weight. The mixing ratio of the active ingredients can be selected in a considerably broad range, and for example the weight ratio of the component (A) to the component (B), that is, (A)/(B), can be from 100/1 to 1/100, particularly 50/1 to 1/50, especially 20/1 to 1/20. In this weight ratio, the amount of the component (A) is the amount of the agrochemical material (active ingredient of the herbicide) contained in the amino acid-based herbicide.

Preferably, the herbicide composition of the present invention further contains at least one surfactant selected from the group consisting of (C) a cationic surfactant, an anionic surfactant and an amphoteric surfactant (referred to hereinafter as component (C)).

Preferably, the cationic surfactant is at least one member selected from the group consisting of a quaternary ammonium salt represented by the general formula (2):

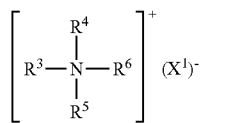
(2)

wherein $R^3$ represents a C8 to C30 branched or linear alkyl or alkenyl group, $R^4$ and $R^5$ each represent a hydrogen atom, a C1 to C3 alkyl group or $-(A^1O)_mH$, $A^1$ represents a C2 to C4 alkylene group, m is a mean number in the range of 1 to 15, $R^6$ represents a C1 to C30 branched or linear alkyl or alkenyl group or a benzyl group, and $(X^1)^-$ is a counterion, and a tertiary amine represented by the following general formula (3):

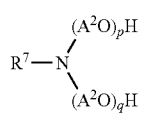
(3)

wherein $R^7$ represents a C1 to C30 branched or linear alkyl or alkenyl group, $A^2$ represents a C2 to C4 alkylene group, p is a means number in the range of 1 to 15, q is a mean number in the range of 1 to 15, and p+q is 2 to 30.

The cationic surfactant represented by the general formula (2) is particularly preferably monoalkyl (preferably C8 to C18, particularly preferably C12 to C14) benzyl dimethyl ammonium chloride, polyoxyalkylene monoalkyl (preferably C8 to C18, particularly preferably C12 to C18, and p+q is preferably 2 to 20, particularly preferably p+q is 2 to 15) monomethyl ammonium chloride, dialkyl (preferably C8 to C18, particularly preferably C10 to C14) dimethyl ammonium chloride, monoalkyl (preferably C8 to C18, particularly preferably C12 to C18) trimethyl ammonium chloride, or polyoxyalkylene monoalkyl (preferably C8 to C18, particularly preferably C12 to C14, and preferably p+q is 2 to 20, and particularly preferably p+q is 2 to 15) benzyl ammonium chloride. The counterion is preferably a halogen ion or an alkyl sulfate ion.

The cationic surfactant of the general formula (3) is particularly preferably polyoxyalkylene (preferably polyoxyethylene, and preferably p+q is 2 to 20, particularly preferably p+q=2 to 15) monoalkyl (preferably C8 to C22, particularly preferably C12 to C18)amine.

The anionic surfactant includes sodium mono- and di-alkyl naphthalene sulfonates, sodium α-olefin sulfonates, sodium alkane sulfonate, alkyl sulfosuccinates, alkyl sulfates, polyoxyalkylene alkyl ether sulfates, polyoxyalkylene alkyl aryl ether sulfates, polyoxyalkylene styryl phenyl ether sulfates, mono- and di-alkyl benzene sulfonates, alkyl naphthalene sulfonates, alkyl naphthalene sulfonate/formaldehyde condensates, alkyl diphenyl ether sulfonates, olefinic sulfonates, mono- and di-alkyl phosphates, polyoxyalkylene mono- and di-alkyl phosphates, polyoxyalkylene mono- and di-phenyl ether phosphates, polyoxyalkylene mono- and di-alkyl phenyl ether phosphates, polycarboxylates, fatty acid salts, linear and branched alkyl polyoxyalkylene ether acetic acid or its salts, alkenyl polyoxyalkylene ether acetic acid or its salts, stearic acid and its salts, oleic acid and its salts, N-methyl fatty acid taurides, and mixtures of two or more thereof (including sodium, potassium, ammonium and amine salts).

Preferably, the anionic surfactant is at least one member selected from the group consisting of an alkyl sulfonate represented by the following general formula (4):

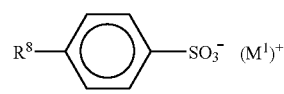
(4)

wherein $R^8$ represents a C6 to C30 branched or linear alkyl or alkenyl group, and $(M^1)^+$ is a counterion, an ether acetate represented by the following general formula (5):

$$R^9O(A^3O)_rCH_2COO^-(M^2)^+ \quad (5)$$

wherein $R^9$ represents a C6 to C30 branched or linear alkyl or alkenyl group, $A^3$ represents a C2 to C4 alkylene group, r is a mean number in the range of 1 to 30, and $(M^2)^+$ is a counterion, and an ether sulfate represented by the following general formula (6):

$$R^{10}O(A^4O)_tSO_3^-(M^3)^+ \quad (6)$$

wherein $R^{10}$ represents a C6 to C30 branched or linear alkyl or alkenyl group, $A^4$ represents a C2 to C4 alkylene group, t is a mean number in the range of 0 to 30, and $(M^3)^+$ is a counterion.

The anionic surfactant of the general formula (4) is particularly preferably an alkyl benzene sulfonate.

The anionic surfactant of the general formula (5) is particularly preferably a polyoxyethylene alkyl ether acetate.

The anionic surfactant of the general formula (6) is particularly preferably a polyoxyethylene alkyl ether sulfate.

Preferably, the amphoteric surfactant is at least one member selected from the group consisting of an alkyl hydroxy sulfobetaine represented by the following general formula (7):

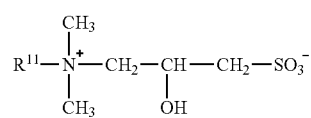
(7)

wherein $R^{11}$ represents a C6 to C30 branched or linear alkyl or alkenyl group, a 2-alkyl-N-carboxymethyl-N-hydroxyethyl imidazolium betaine represented by the following formula (8):

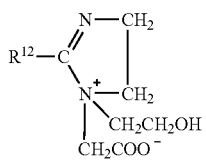
(8)

wherein $R^{12}$ represents a C6 to C30 branched or linear alkyl or alkenyl group, an amide propyl betaine represented by the following general formula (9):

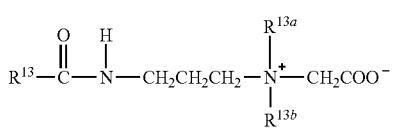
(9)

wherein $R^{13}$ represents a C6 to C30 branched or linear alkyl or alkenyl group, $R^{13a}$ and $R^{13b}$ each represent a methyl group or $(A^5O)_vH$, $A^5$ is a C2 to C4 alkylene group, and v is a mean number in the range of 1 to 30, and an alkyl acetic acid betaine represented by the following general formula (10):

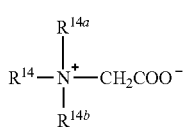
(10)

wherein $R^{14}$ represents a C6 to C30 branched or linear alkyl or alkenyl group, $R^{14a}$ and $R^{14b}$ each represent a methyl group or $(A^6O)_wH$, $A^6$ represents a C2 to C4 alkylene group, and w is a mean number in the range of 1 to 30.

In the general formula (7), $R^{11}$ is preferably a C8 to C18 group, more preferably a C12 to C14 group.

In the general formula (8), $R^{12}$ is preferably a C8 to C18 group, more preferably a C12 to C14 group.

In the general formula (9), $R^{13}$ is preferably a C8 to C18 group, more preferably a C12 to C14 group, and each of $R^{13a}$ and $R^{13b}$ is preferably a methyl group.

In the general formula (10), $R^{14}$ is preferably a C8 to C18 group, more preferably a C12 to C14 group, and each of $R^{14a}$ and $R^{14b}$ is preferably a methyl group.

The herbicide composition of the present invention preferably contains the component (C) in an amount of 0.01 to 80% by weight, particularly 0.1 to 50% by weight.

If necessary, a pH adjusting agent, inorganic salts and a thickener may be added to the herbicide composition of the present invention. The pH adjusting agent which can be used in the present invention is citric acid, phosphoric acid (pyrophosphoric acid), gluconic acid, or salts thereof. The inorganic salts which can be used in the present invention include inorganic ammonium salts such as ammonium sulfate, ammonium nitrate, ammonium phosphate, ammonium thiocyanate, ammonium chloride and ammonium sulfamate.

As the herbicide composition of the present invention, the raw chemical itself is applied as it is, or is mixed with carriers and other additives if necessary for use in preparation forms usually used as herbicides, for example in forms such as powder, coarse powder, fine particle, particle, wetting agent, granular wetting agent, emulsion, liquid, aqueous solution, water-soluble agent (so-called jumbo agent), flowable agent, microcapsule, oil suspension etc. For use, these preparations can also be mixed with a plurality of other herbicides, insecticides, bactericides, plant growth regulators and fertilizers. The preparation can be compounded particularly with one or more kinds of other herbicides to broaden its herbicidal spectrum or maintain its efficacy for a longer time.

The solid carriers usable for preparing the herbicide composition of the present invention include, for example, inorganic materials such as clays represented by kaolinite, montmorillonite or attapulgite, and talc, mica, chemical agalmatolite, fluorite, vermiculite gypsum, calcium carbonate, dolomite, diatomaceous earth, magnesium, lime, calcium phosphate, zeolite, anhydrous silicic acid, synthetic silicic acid, calcium, etc.; vegetable organic materials such as soybean powder, tobacco powder, walnut powder, wheat powder, wood powder, soybean flour, starch, crystalline cellulose, etc.; inorganic or organic substances such as potassium chloride, sodium chloride, ammonium chloride, ammonium sulfate, ammonium nitrate, urea, citric acid, sodium citrate, sodium tartrate, glucose, fructose, etc.; synthetic or natural polymer compounds such as chroman resin, petroleum resin, alkyd resin, polyvinyl chloride, polyalkylene glycol, ketone resin, ester gum, copal gum, dammar gum, etc.; wax such as carnauba wax, beeswax, etc.; urea etc.

The liquid carrier which can be used in preparing the herbicide composition of the present invention includes paraffin- or naphthyne-based hydrocarbons such as kerosine, mineral oil, spindle oil, white oil, etc.; alcohols such as methanol, n-hexanol, ethylene glycol, diethylene glycol, cyclohexanol, benzyl alcohol, etc.; ether alcohols such as ethylene glycol ethyl ether, ethylene glycol phenyl ether, diethylene glycol ethyl ether, diethylene glycol butyl ether, etc.; fatty alcohol esters such as methyl oleate, butyl oleate, isopropyl myristate, palm fatty acid, etc.; polybasic alcohol esters such as diisobutyl adipate, ditridecyl phthalate, dialkyl(C10-C12) phthalate, dialkyl(C8,C10) phthalate, etc.; water, etc.

For preparing a pharmaceutical preparation from the herbicide composition of the present invention, water-soluble polymers and surfactants such as the surfactant as component (C) and nonionic surfactants other than component (B) can be used. The water-soluble polymers include, for example, polyvinyl alcohol, carboxymethyl cellulose, alginate, polyacrylate, starch, enzymatically decomposed dextrin, or isobutyl maleate copolymers salts (Na salt, K salt, Ca salt, ammonium salt, various amine salts etc.) known under the trade names Isoban 1-1, 1-2, 1-3, 2-1, 2-2, 2-3, 3-1, 3-2, 3-3, SF-837, and SF-842 (all of which are manufactured by Kuraray Isoprene Chemical). Depending on the case, a cationic surfactant and an amphoteric surfactant can also be used.

The surfactants described above can be used alone or as a mixture of two or more thereof. The granular composition may be compounded if necessary with suitable amounts of other additives used usually in agrochemicals, for example with a spreading agent, a preservative, an emulsifier, a decomposition inhibitor, a solidification inhibitor, an activity enhancer (for example, soybean lecithin or vegetable oil) etc., and if necessary mixed with, and used in combination with, agrochemical components such as insecticides, miticides, nematocides, bactericides, antiviral agents, inducers, plant growth regulators, fertilizers etc.

According to the present invention, there is provided an efficacy enhancer composition for a herbicide particularly an amino acid-based herbicide, which further contains the components (B) and (C) described above. In the composition, the component (B) is contained in an amount of preferably 0.01 to 50% by weight, more preferably 0.1 to 20% by weight, and the component (C) is contained in an amount of preferably 0.01 to 80% by weight, more preferably 0.1 to 50% by weight, the balance being water.

EXAMPLES

Hereinafter, the present invention is described in more detail by reference to the Examples. The examples are described for merely illustrating the present invention and not intended to limit the present invention.

<Efficacy Enhancer Composition>

The efficacy enhancer compositions (Nos. 1 to 19) used in the Examples and Comparative Examples below were prepared from the component (B), component (C) etc. shown in Table 1. In the table, POE is an abbreviation of polyoxyethylene, POP is an abbreviation of polyoxypropylene, and the number in the brackets is the average number of units added.

TABLE 1

| | | | Product of the invention | | | | | | | | | | |
|---|---|---|---|---|---|---|---|---|---|---|---|---|---|
| | | Efficacy enhancer No. | 1 | 2 | 3 | 4 | 5 | 6 | 7 | 8 | 9 | 10 |
| Composition (weight-%) | Component (B) | POP(6)POE(3)2-ethyl hexyl ether | 35 | 5 | | | | | | | | 5 |
| | | POE(12) isotridecyl ether *1 | | | 2 | | | | | | 35 | |
| | | POE(7) isodecyl ether *2 | | | | 35 | 10 | | | | | |
| | | POE(15) Guerbet-alkyl (C$_{28}$) ether | | | | | | 5 | | | | |
| | | POE(5)POP(10) isostearyl ether | | | | | | | 5 | | | |
| | | POP(6)POE(10)2-octyl dodecyl ether | | | | | | | | 5 | | |
| | Component (C) Cationic | POE(20) stearyl amine | | | 20 | 20 | | | | | | |
| | | POE(15) tallow alkyl amine | | | | | | 20 | | | | |
| | | POE(2) cocoalkyl amine | | | | | | | 20 | | | |
| | | Lauryl benzyl dimethyl ammonium chloride | | | 10 | 10 | | | | | | |
| | | Didecyl dimethyl ammonium chloride | | | | | | 10 | | | | |
| | | POE(5) lauryl benzyl ammonium chloride | | | | | 25 | | | | | |
| | | POE(2) cocoalkyl methyl ammonium methyl sulfate | | | | | | | | 10 | | |
| | Anionic | Calcium dodecyl benzene sulfonate | | | | 2 | | | | | | |
| | | Sodium POE(10) lauryl ether acetate | | | | | | | | | 30 | |
| | | Sodium POE(3) lauryl ether sulfate | | | | | | | | | | 30 |
| | Amphoteric | Lauryl hydroxy sulfobetaine | | | | | | | | | | |
| | | 2 Lauryl N-carboxymethylated N-hydroxyethyl imidazolinium betaine | | | | | | | | | | |
| | | Coconut fatty acid amide propyl betaine | | | | | | | | | | |
| | | Lauryl dimethyl aminoacetic acid betaine | | | | | | | | | | |
| | POE(7) secondary C12-C14 alkyl ether *3 | | | | | | | | | | | |
| | POE(9) lauryl ether | | | | | 1 | | | | | | |
| | POE(5)POP(5)POE(5)isostearyl ether | | | | | | | | | | | |
| | Distilled water | | 65 | 65 | 65 | 65 | 65 | 65 | 65 | 65 | 65 | 65 |

| | | | Product of the invention | | | | Comparative product | | | | |
|---|---|---|---|---|---|---|---|---|---|---|---|
| | | Efficacy enhancer No. | 11 | 12 | 13 | 14 | 15 | 16 | 17 | 18 | 19 |
| Composition (weight-%) | Component (B) | POP(6)POE(3)2-ethyl hexyl ether | | | | 2.5 | | | | | |
| | | POE(12) isotridecyl ether *1 | 5 | | 5 | | | | | | |
| | | POE(7) isodecyl ether *2 | | 5 | | | | | | | |
| | | POE(15) Guerbet-alkyl (C$_{28}$) ether | | | | | | | | | |
| | | POE(5)POP(10) isostearyl ether | | | | | | | | | |
| | | POP(6)POE(10)2-octyl dodecyl ether | | | | | | | | | |
| | Component (C) Cationic | POE(20) stearyl amine | | | | 20 | | | 20 | | |
| | | POE(15) tallow alkyl amine | | | | | | 20 | | | |
| | | POE(2) cocoalkyl amine | | | | | | | | | |
| | | Lauryl benzyl dimethyl ammonium chloride | | | | 10 | | 10 | 10 | | |
| | | Didecyl dimethyl ammonium chloride | | | | | | | | | |
| | | POE(5) lauryl benzyl ammonium chloride | | | | | | | | | |
| | | POE(2) cocoalkyl methyl ammonium methyl sulfate | | | | | | | | | |
| | Anionic | Calcium dodecyl benzene sulfonate | | | | | | | | | |
| | | Sodium POE(10) lauryl ether acetate | | | | | | | | | |
| | | Sodium POE(3) lauryl ether sulfate | | | | | | | | | |
| | Amphoteric | Lauryl hydroxy sulfobetaine | 30 | | | | | | | | |
| | | 2 Lauryl N-carboxymethylated N-hydroxyethyl imidazolinium betaine | | 30 | | | | | | | |
| | | Coconut fatty acid amide propyl betaine | | | 30 | | | | | | |
| | | Lauryl dimethyl aminoacetic acid betaine | | | | 2.5 | | | 2.5 | | |
| | POE(7) secondary C12-C14 alkyl ether *3 | | | | | | 35 | 5 | | | |
| | POE(9) lauryl ether | | | | | | | | 2.5 | 35 | |
| | POE(5)POP(5)POE(5)isostearyl ether | | | | | | | | | | 35 |
| | Distilled water | | 65 | 65 | 65 | 65 | 65 | 65 | 65 | 65 | 65 |

*1 Ethylene oxide (referred to hereinafter as EO) adduct (average number of EO units added: 12) of Isotridecanol (trade name: Exxal 13 manufactured by Exxon Mobile)
*2 EO adduct (average number of EO units added: 7) of Isodecanol (trade name: Decanol manufactured by Kyowa Hakko Chemical)
*3 EO adduct (average number of EO units added: 7) of C12 to C14 secondary alcohol (trade name: EMULGEN manufactured by Kao Corporation)

Example 1

Herbicide compositions (glyphosate preparations) containing 10 wt % efficacy enhancers in Table 1 and 41 wt % glyphosate isopropyl amine salt, the balance being water (distilled water), were prepared. The permeability and herbicidal efficacy were evaluated by the following methods.

<Permeability>

100 mL aqueous solution prepared by diluting the glyphosate preparation 10-fold with tap water was placed in a 100-mL beaker, and a cotton cloth (2 cm×2 cm) was allowed to float gently thereon, and the time (seconds) having elapsed until the cotton cloth sunk completely in the solution was measured to examine the permeability of each formulation. The results are shown in Table 2.

TABLE 2

| | Preparation No. | Efficacy enhancer No. | Sinking time (seconds) |
|---|---|---|---|
| Product of the invention | 1-1 | 1 | 130 |
| | 1-2 | 2 | 122 |
| | 1-3 | 3 | 140 |
| | 1-4 | 4 | 150 |
| | 1-5 | 5 | 150 |
| | 1-6 | 6 | 170 |
| | 1-7 | 7 | 160 |
| | 1-8 | 8 | 156 |
| | 1-9 | 9 | 132 |
| | 1-10 | 10 | 165 |
| | 1-11 | 11 | 159 |
| | 1-12 | 12 | 154 |
| | 1-13 | 13 | 131 |
| | 1-14 | 14 | 162 |
| Comparative product | 1-1 | 15 | 209 |
| | 1-2 | 16 | 235 |
| | 1-3 | 17 | 300 |
| | 1-4 | 18 | 280 |
| | 1-5 | 19 | 215 |

As can be seen from the results in Table 2, the products of the invention (Nos. 1 to 14) containing a primary alkoxylate having a branched chain have higher wetting properties and permeability than those of the preparation containing a linear primary alkoxylate or the preparation having a secondary alkoxylate.

<Herbicidal Efficacy Test>

For a greenhouse test, fertile soil collected from a paddy field, river sand, and commercial compost were mixed in a ratio of 7:2:1 (weight ratio) and then placed in pots of 12 cm in inner diameter, and crabgrass seeds were sown in each pot and germinated. Pots where the crabgrass grew to reach about 18 cm in height were selected and used in the test. An aqueous solution was prepared by diluting the above glyphosate preparation 200-fold with tap water, and then sprayed uniformly onto the whole of the crabgrass by a spray gun (RG type, manufactured by Iwata Tosou Kogyo) in a proportion of 50 L/10 a, to evaluate the herbicidal efficacy. In evaluation of herbicidal efficacy, the weight of the crabgrass over the ground was measured 10 days after the spraying treatment and a herbicidal ratio (%) was determined in relation to the weight of the crabgrass over the ground in an untreated group. The herbicidal ratio by each preparation is shown in Table 3.

TABLE 3

| | Preparation No. | Herbicidal ratio (%) |
|---|---|---|
| Product of the invention | 1-1 | 80.5 |
| | 1-2 | 97.6 |
| | 1-3 | 94.3 |
| | 1-4 | 81.0 |
| | 1-5 | 92.5 |
| | 1-6 | 90.3 |
| | 1-7 | 92.4 |
| | 1-8 | 80.5 |
| | 1-9 | 81.3 |
| | 1-10 | 80.2 |
| | 1-11 | 82.5 |
| | 1-12 | 82.5 |
| | 1-13 | 85.5 |
| | 1-14 | 80.6 |
| Comparative product | 1-1 | 65.2 |
| | 1-2 | 72.5 |
| | 1-3 | 70.0 |
| | 1-4 | 72.5 |
| | 1-5 | 70.5 |

Example 2

Herbicide compositions (glyphosate preparations) containing 10 wt % efficacy enhancer in Table 1 and 18.5 wt % glyphosate, the balance being water (distilled water), were prepared, and the herbicidal efficacy test (herbicidal ratio) was conducted in the same manner as in Example 1. The results are shown in Table 4.

TABLE 4

| | Preparation No. | Efficacy enhancer No. | Herbicidal ratio (%) |
|---|---|---|---|
| Product of the invention | 2-1 | 1 | 74.8 |
| | 2-2 | 2 | 82.5 |
| | 2-3 | 3 | 82.0 |
| | 2-4 | 4 | 76.5 |
| | 2-5 | 5 | 80.3 |
| | 2-6 | 6 | 79.8 |
| | 2-7 | 7 | 80.6 |
| | 2-8 | 8 | 92.5 |
| | 2-9 | 9 | 73.2 |
| | 2-10 | 10 | 90.8 |
| | 2-11 | 11 | 89.5 |
| | 2-12 | 12 | 90.8 |
| | 2-13 | 13 | 88.9 |
| | 2-14 | 14 | 85.6 |
| Comparative product | 2-1 | 15 | 58.5 |
| | 2-2 | 16 | 60.4 |
| | 2-3 | 17 | 62.1 |
| | 2-4 | 18 | 55.6 |
| | 2-5 | 19 | 52.5 |

The invention claimed is:

1. A herbicide composition comprising (A) an amino acid-based herbicide and (B) a compound represented by the following general formula (1'):

$$R^1CH_2O\text{---}(R^{2a}O)_j(R^{2b}O)_kH \quad (1')$$

wherein $R^1$ represents a C3 to C29 branched alkyl group and the branched chain type of $R^1CH_2$— is Guerbet or iso, $R^{2a}$ and $R^{2b}$ each represent a C2 to C4 alkylene group, and are not simultaneously the same, j and k each represent a mean number in the range of 0 to 30, and are not simultaneously 0, j+k=6 to 20, and $R^{2a}O$ and $R^{2b}O$ are added in a block form.

2. The herbicide composition according to claim 1, which comprises at least one member selected from the group consisting of (C) a cationic surfactant, an anionic surfactant and an amphoteric surfactant.

3. The herbicide composition according to claim 2, wherein the cationic surfactant is at least one member selected from the group consisting of a quaternary ammonium salt represented by the general formula (2):

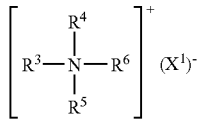 (2)

wherein $R^3$ represents a C8 to C30 branched or linear alkyl or alkenyl group, $R^4$ and $R^5$ each represent a hydrogen atom, a C1 to C3 alkyl group or $-(A'O)_mH$, $A^1$ represents a C2 to C4 alkylene group, m is a mean number in the range of 1 to 15, $R^6$ represents a C1 to C30 branched or linear alkyl or alkenyl group or a benzyl group, and $(X^1)^-$ is a counterion, and a tertiary amine represented by the following general formula (3):

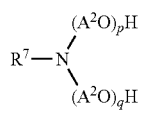 (3)

wherein $R^7$ represents a C1 to C30 branched or linear alkyl or alkenyl group, $A^2$ represents a C2 to C4 alkylene group, p is a mean number in the range of 1 to 15, q is a mean number in the range of 1 to 15, and p+q is 2 to 30.

4. The herbicide composition according to claim 2, wherein the anionic surfactant is at least one member selected from the group consisting of an alkyl sulfonate represented by the following general formula (4):

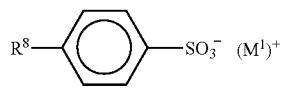 (4)

wherein $R^8$ represents a C6 to C30 branched or linear alkyl or alkenyl group, and $(M^1)^+$ is a counterion, an ether acetate represented by the following general formula (5):

$$R^9O(A^3O)_rCH_2COO^-(M^2)^+ \quad (5)$$

wherein $R^9$ represents a C6 to C30 branched or linear alkyl or alkenyl group, $A^3$ represents a C2 to C4 alkylene group, r is a mean number in the range of 1 to 30, and $(M^2)^+$ is a counterion, and an ether sulfate represented by the following general formula (6):

$$R^{10}O(A^4O)_tSO_3^-(M^3)^+ \quad (6)$$

wherein $R^{10}$ represents a C6 to C30 branched or linear alkyl or alkenyl group, $A^4$ represents a C2 to C4 alkylene group, t is a mean number in the range of 0 to 30, and $(M^3)^+$ is a counterion.

5. The herbicide composition according to claim 2, wherein the amphoteric surfactant is at least one member selected from the group consisting of an alkyl hydroxy sulfobetaine represented by the following general formula (7):

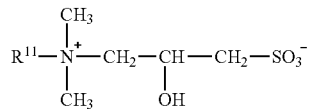 (7)

wherein $R^{11}$ represents a C6 to C30 branched or linear alkyl or alkenyl group, a 2-alkyl-N-carboxymethyl-N-hydroxyethyl imidazolium betaine represented by the following formula (8):

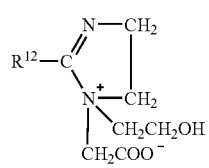 (8)

wherein $R^{12}$ represents a C6 to C30 branched or linear alkyl or alkenyl group, an amide propyl betaine represented by the following general formula (9):

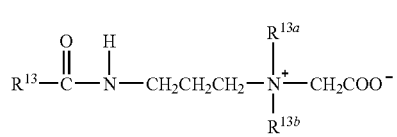 (9)

wherein $R^{13}$ represents a C6 to C30 branched or linear alkyl or alkenyl group, $R^{13a}$ and $R^{13b}$ each represent a methyl group or $(A^5O)_vH$, $A^5$ is a C2 to C4 alkylene group, and v is a mean number in the range of 1 to 30, and an alkyl acetic acid betaine represented by the following general formula (10):

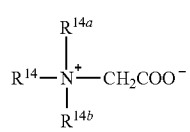 (10)

wherein $R^{14}$ represents a C6 to C30 branched or linear alkyl or alkenyl group, $R^{14a}$ and $R^{14b}$ each represent a methyl group or $(A^6O)_wH$, $A^6$ represents a C2 to C4 alkylene group, and w is a mean number in the range of 1 to 30.

6. An efficacy enhancer composition for a herbicide, which comprises (B) a compound represented by the general formula (1'):

$$R^1CH_2O-(R^{2a}O)_j(R^{2b}O)_kH \quad (1')$$

wherein $R^1$ represents a C3 to C29 branched alkyl group and the branched chain type of $R^1CH_2-$ is Guerbet or iso, $R^{2a}$ and $R^{2b}$ each represent a C2 to C4 alkylene group, and are not simultaneously the same, j and k each represent a mean number in the range of 0 to 30, and are not simultaneously 0, j+k=6 to 20, and $R^{2a}O$ and $R^{2b}O$ are added in a block form.

7. The efficacy enhancer composition for a herbicide according to claim 6, which further comprises at least one member selected from the group consisting of (C) a cationic surfactant, an anionic surfactant and an amphoteric surfactant.

8. A method of weeding a plant to weed, comprising applying the composition of claim 1 onto the plant.

9. A method of enhancing the efficacy of a herbicide, comprising the step of adding the compound (B) of claim 6 to said herbicide.

10. The herbicide composition according to claim 1, wherein $R^1CH_2$— is selected from the group consisting of a 2-ethylhexyl group, an isotridecyl group, an isodecyl group, a C28 Guerbet-alkyl group, an isostearyl group, and a 2-octyldodecyl group.

11. The efficacy enhancer composition for a herbicide according to claim 6, wherein $R^1CH_2$— is selected from the group consisting of a 2-ethylhexyl group, an isotridecyl group, an isodecyl group, a C28 Guerbet-alkyl group, an isostearyl group, and a 2-octyldodecyl group.

* * * * *